United States Patent
Miyagawa et al.

(10) Patent No.: US 10,208,643 B2
(45) Date of Patent: Feb. 19, 2019

(54) PARTICULATE MATTER DETECTION APPARATUS

(71) Applicant: DENSO CORPORATION, Kariya, Aichi-pref. (JP)

(72) Inventors: Go Miyagawa, Kariya (JP); Hirokatsu Imagawa, Kariya (JP); Masayuki Tamura, Kariya (JP)

(73) Assignee: DENSO CORPORATION, Kariya (JP)

( * ) Notice: Subject to any disclaimer, the term of this patent is extended or adjusted under 35 U.S.C. 154(b) by 16 days.

(21) Appl. No.: 15/319,541

(22) PCT Filed: Jun. 12, 2015

(86) PCT No.: PCT/JP2015/066978
§ 371 (c)(1),
(2) Date: Dec. 16, 2016

(87) PCT Pub. No.: WO2015/194468
PCT Pub. Date: Dec. 23, 2015

(65) Prior Publication Data
US 2017/0122179 A1 May 4, 2017

(30) Foreign Application Priority Data

Jun. 16, 2014 (JP) .................................. 2014-123664
Feb. 17, 2015 (JP) .................................. 2015-028846

(51) Int. Cl.
*F01N 11/00* (2006.01)
*G01N 15/06* (2006.01)
(Continued)

(52) U.S. Cl.
CPC ............ *F01N 11/002* (2013.01); *F01N 3/021* (2013.01); *F02D 41/061* (2013.01);
(Continued)

(58) Field of Classification Search
CPC .... F10N 11/002; F10N 3/021; F10N 2330/06; F10N 2560/06; F10N 2560/05; F10N 2900/1404; G01N 27/04
See application file for complete search history.

(56) References Cited

U.S. PATENT DOCUMENTS 8,230,716 B2 * 7/2012 Nelson ................ F02D 41/1466
324/693
8,438,899 B2 * 5/2013 Zawacki ............. F02D 41/1494
701/30.9
(Continued)

FOREIGN PATENT DOCUMENTS

JP 3-238046 10/1991
JP 5-163934 6/1993
(Continued)

OTHER PUBLICATIONS

International Search Report dated Aug. 25, 2015 issued in corresponding JP Application No. PCT/JP2015/066978 with English translation (2 pages).

*Primary Examiner* — Julian D Huffman
*Assistant Examiner* — Michael T Konczal
(74) *Attorney, Agent, or Firm* — Nixon & Vanderhye P.C.

(57) ABSTRACT

A particulate matter detection apparatus includes a particulate matter quantity detection means, a temperature detection means that detects the temperature of exhaust gas, a control unit and a heating means. The particulate matter quantity detection means includes a particulate matter deposition portion that deposits thereon part of particulate matter contained in the exhaust gas emitted from an internal combustion engine and a pair of opposite electrodes arranged apart from each other on the particulate matter deposition portion. The control unit determines a deposition quantity of the particulate matter on the particulate matter deposition portion based on an electrical signal outputted by (Continued)

the particulate matter quantity detection means and receives information on the temperature of the exhaust gas detected by the temperature detection means. The control unit controls the heating means to heat the particulate matter deposition portion to 300° C.-800° C. during a cold start of the internal combustion engine.

5 Claims, 4 Drawing Sheets

(51) Int. Cl.
  *F01N 3/021* (2006.01)
  *G01N 27/04* (2006.01)
  *F02D 41/06* (2006.01)
  *F02D 41/14* (2006.01)
  *F02D 41/22* (2006.01)
  *G01N 15/00* (2006.01)

(52) U.S. Cl.
  CPC ....... *F02D 41/064* (2013.01); *F02D 41/1446* (2013.01); *F02D 41/1466* (2013.01); *F02D 41/1494* (2013.01); *F02D 41/222* (2013.01); *G01N 15/0606* (2013.01); *G01N 15/0656* (2013.01); *G01N 27/04* (2013.01); *F01N 2330/06* (2013.01); *F01N 2560/05* (2013.01); *F01N 2560/06* (2013.01); *F01N 2900/1404* (2013.01); *G01N 2015/0046* (2013.01); *Y02T 10/40* (2013.01)

(56) References Cited

U.S. PATENT DOCUMENTS

| | | | |
|---|---|---|---|
| 9,617,899 B2* | 4/2017 | Goodwin | F01N 11/007 |
| 2009/0116534 A1* | 5/2009 | Tabery | G01N 27/4118 |
| | | | 374/45 |
| 2011/0314796 A1* | 12/2011 | Nakamura | F01N 9/002 |
| | | | 60/276 |
| 2014/0238108 A1 | 8/2014 | Di Miro et al. | |

FOREIGN PATENT DOCUMENTS

| | | | |
|---|---|---|---|
| JP | 2011-080926 | | 4/2011 |
| JP | 2011080926 A | * | 4/2011 |

* cited by examiner

PARTICULATE MATTER DETECTION APPARATUS

This application is the U.S. national phase of International Application No. PCT/JP2015/066978 filed 12 Jun. 2015 which designated the U.S. and claims priority to JP Patent Application No. 2014-123664 filed 16 Jun. 2014 and JP Patent Application No. 2015-028846 filed 17 Feb. 2015, the entire contents of each of which are hereby incorporated by reference.

TECHNICAL FIELD

The present invention relates to particulate matter detection apparatuses that detect the quantity of particulate matter contained in exhaust gas produced in an internal combustion engine.

BACKGROUND ART

In an exhaust pipe of an internal combustion engine, there is provided an exhaust gas purifying apparatus that traps Particulate Matter (PM) contained in the exhaust gas. The exhaust gas purifying apparatus includes a particulate matter detection apparatus having a PM sensor to detect the quantity of particulate matter contained in the exhaust gas. Based on information obtained by the particulate matter detection apparatus, a failure detection of the exhaust gas purifying apparatus is performed.

The PM sensor employed in the particulate matter detection apparatus is configured so that for a time period from the completion of detection of particulate matter to the next detection, the PM sensor is heated to burn off the particulate matter having adhered to the PM sensor.

However, during a cold start of the internal combustion engine, condensate water, which is produced by the condensation of moisture in the exhaust gas, may adhere to the PM sensor. If the adhering timing of the condensate water coincides with the aforementioned heating timing of the PM sensor, water-induced cracking of the PM sensor may be caused. Therefore, in the particulate matter detection apparatus disclosed in Patent Document 1, for a predetermined time period during a cold start of the engine, heating of the PM sensor for burning off the particulate matter is not performed.

PRIOR ART LITERATURE

Patent Literature

[PATENT DOCUMENT 1] Japanese Patent Application Publication No. JP2012012960A

SUMMARY OF THE INVENTION

Problems to be Solved by the Invention

However, the particulate matter detection apparatus disclosed in Patent Document 1 has the following problems.

In the particulate matter detection apparatus disclosed in Patent Document 1, when the PM sensor is exposed to water in a state of being not heated, the condensate water adheres to the surface of the PM sensor. The condensate water may include fuel, engine oil or metal components of the exhaust pipe. Therefore, when the condensate water having adhered to the PM sensor is dried, the inclusions of the condensate water may remain on the surface of the PM sensor. These residues may cause malfunction or false detection by the PM sensor.

The present invention has been made in view of the above circumstances, and aims to provide a particulate matter detection apparatus capable of suppressing water-induced cracking and the adherence of condensate water in a particulate matter quantity detection means.

Means for Solving the Problems

A particulate matter detection apparatus according to the present invention includes: a particulate matter quantity detection means including a particulate matter deposition portion that deposits thereon part of particulate matter contained in exhaust gas emitted from an internal combustion engine and a pair of opposite electrodes arranged apart from each other on the particulate matter deposition portion, the particulate matter quantity detection means varying output of an electrical signal according to change in electrical characteristics caused by the deposition of the particulate matter on the particulate matter deposition portion;

a temperature detection means that detects temperature of the exhaust gas or an exhaust pipe through which the exhaust gas flows;

a control unit that determines a deposition quantity of the particulate matter on the particulate matter deposition portion based on the electrical signal outputted by the particulate matter quantity detection means and receives information on the temperature of the exhaust gas or the exhaust pipe detected by the temperature detection means; and a heating means for heating the particulate matter deposition portion, wherein the control unit controls the heating means to heat the particulate matter deposition portion to 300° C.-800° C. during a cold start of the internal combustion engine where the temperature of the exhaust gas detected by the temperature detection means is lower than or equal 100° C. or the temperature of the exhaust pipe detected by the temperature detection means is lower than or equal 60° C.

Advantageous Effects of the Invention

In the above particulate matter detection apparatus, the control unit controls the heating means to heat the particulate matter deposition portion to 300° C.-800° C. during a cold start of the internal combustion engine. Consequently, it is possible to suppress water-induced cracking and the adherence of condensate water in the particulate matter quantity detection means. That is, by heating the particulate matter deposition portion to 300° C.-800° C., it is possible to cause the Leidenfrost effect between the particulate matter deposition portion and the condensate water.

The Leidenfrost effect is a phenomenon in which: at an area where a solid heated to a predetermined temperature or more and a liquid are in contact with each other, the liquid vaporizes to form a vapor film; and the solid and the liquid are caused by the vapor film to be no longer in contact with each other. In the above particulate matter detection apparatus, by heating the particulate matter deposition portion to 300° C.-800° C., the Leidenfrost effect is caused between the particulate matter deposition portion and the condensate water, rendering the particulate matter deposition portion and the condensate water no longer in contact with each other. Moreover, since the coefficient of friction between the condensate water floating on the vapor film and the particulate matter deposition portion is small, the condensate water can easily move along the surface of the particulate matter deposition portion.

Therefore, when the heated particulate matter deposition portion is exposed to water, due to the Leidenfrost effect, the condensate water will easily slip off the particulate matter deposition portion. Hence, it is possible to prevent the condensate water from adhering to the particulate matter deposition portion and thus possible to suppress the particulate matter deposition portion from being suddenly cooled by adherence of the condensate water thereto. Consequently, it is possible to suppress various components included in the condensate water from adhering to the particulate matter deposition portion as residues and water-induced cracking from occurring in the particulate matter deposition portion.

As above, the particulate matter detection apparatus can suppress water-inducted cracking and the adherence of residues in the particulate matter quantity detection means.

EMBODIMENTS FOR CARRYING OUT THE INVENTION

In the above particulate matter detection apparatus, it is preferable for the particulate matter quantity detection means to vary the output of the electrical signal according to change in electrical resistance between the pair of opposite electrodes. The particulate matter quantity detection means that is of an electrical resistance type using change in the electrical resistance value between the pair of opposite electrodes has higher detection accuracy of the particulate matter and less variation than particulate matter quantity detection means of other types. Consequently, it is possible to further improve the accuracy of detecting the deposition quantity of the particulate matter.

Moreover, it is preferable that the heating of the particulate matter deposition portion by the heating means is continued until the elapse of a predetermined operation time from the start of the internal combustion engine. In this case, by continuing the heating until the predetermined operation time at which condensate water is no longer produced in the exhaust gas, it is possible to reliably prevent water-induced cracking and the adherence of condensate water in the particulate matter deposition portion.

Moreover, the heating temperature of the particulate matter deposition portion by the heating means is set to 300° C.-800° C. If the heating temperature by the heating means was lower than 300° C., the Leidenfrost effect might be not caused between the particulate matter deposition portion and the condensate water and thus the condensate water might come to adhere to the particulate matter deposition portion. On the other hand, if the heating temperature by the heating means was higher than 800° C., water-induced cracking might occur even though the Leidenfrost effect might be caused.

Moreover, it is preferable for the heating temperature of the particulate matter deposition portion by the heating means to be set to 400° C.-700° C. In this case, it is possible to further improve the effects of suppressing the adherence of condensate water and suppressing occurrence of water-induced cracking.

Examples

A particulate matter detection apparatus according to an example will be described with reference to FIGS. 1-4.

Figure 1:
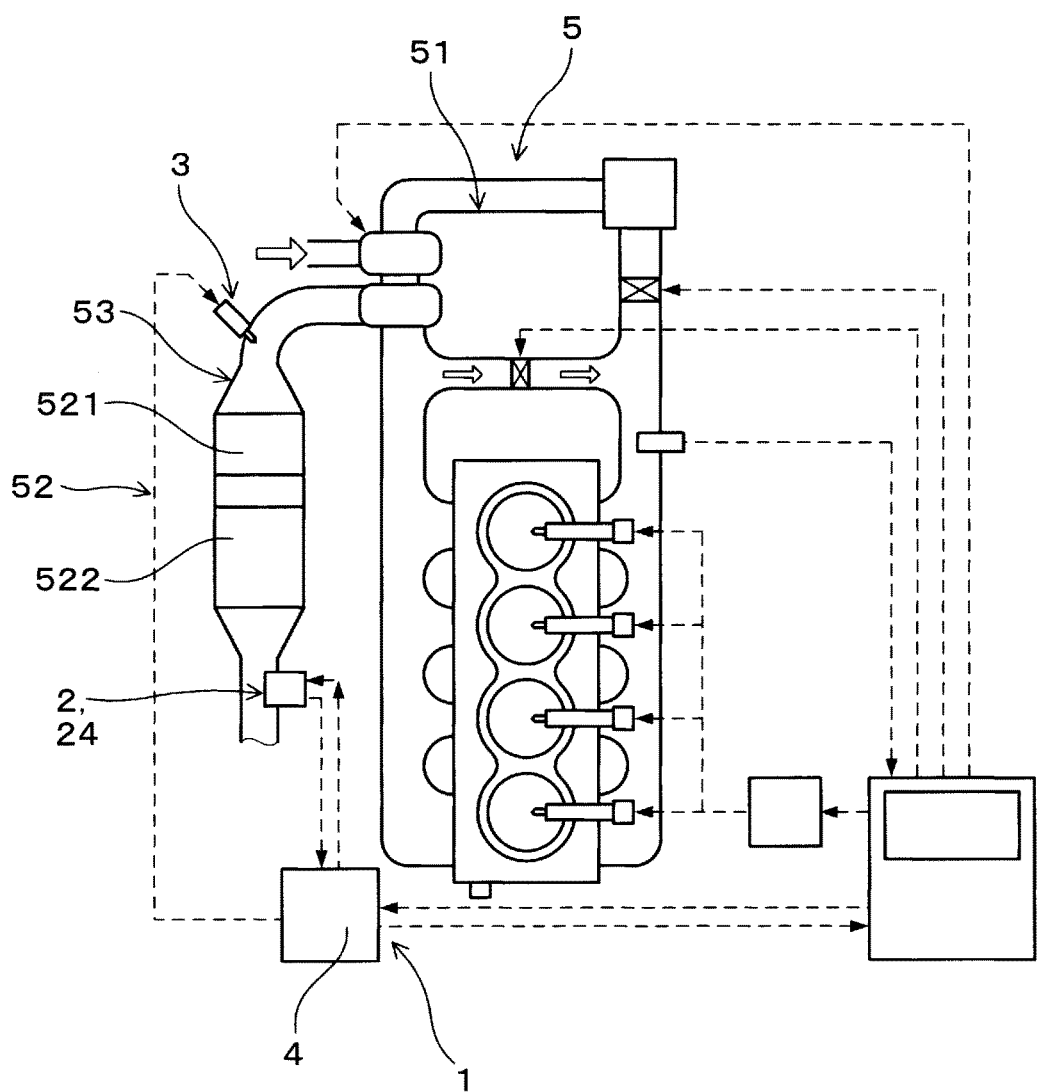
FIG. 1 is a schematic view showing an internal combustion engine which includes a particulate matter detection apparatus according to an example.

As shown in FIG. 1, the particulate matter detection apparatus 1 includes: a particulate matter quantity detection means 2 that varies the output of an electrical signal according to change in electrical characteristics caused by deposition of particulate matter 6 on a particulate matter deposition portion 22; a temperature detection means 3 that detects the temperature of exhaust gas; a control unit 4 that determines the deposition quantity of the particulate matter 6; and a heating means 24 that heats the particulate matter deposition portion 22.

Figure 2:
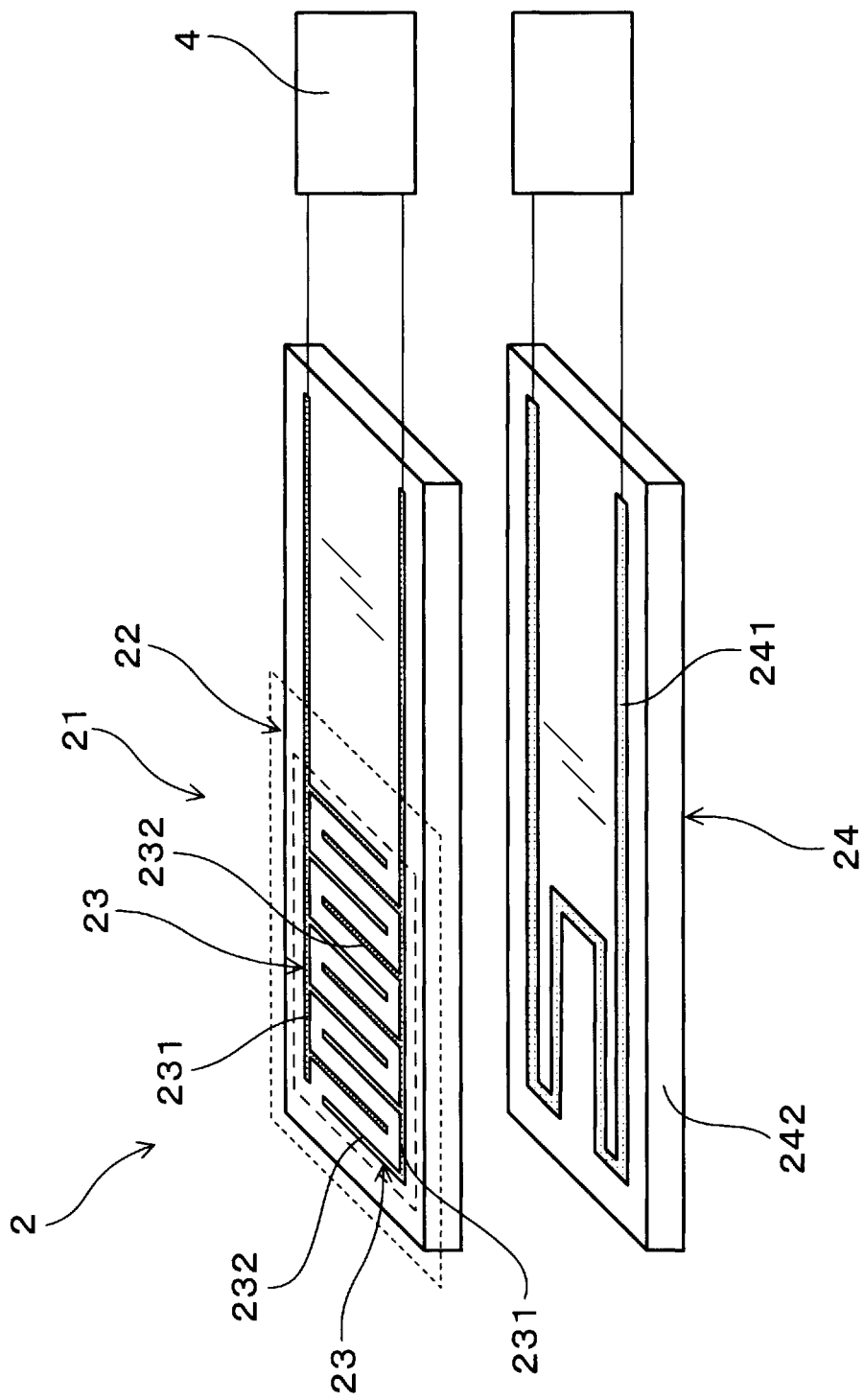
FIG. 2 is a schematic view showing a particulate matter quantity detection means of the particulate matter detection apparatus according to the example.

As shown in FIG. 2, the particulate matter quantity detection means 2 includes: the particulate matter deposition portion 22 that deposits thereon part of the particulate matter 6 contained in the exhaust gas emitted from an internal combustion engine 5; and a pair of opposite electrodes 23 arranged apart from each other on the particulate matter deposition portion 22. The control unit 4 determines the deposition quantity of the particulate matter 6 on the particulate matter deposition portion 22 on the basis of the electrical signal outputted by the particulate matter quantity detection means 2. The control unit 4 also receives information on the temperature of the exhaust gas detected by the temperature detection means 3. Moreover, the control unit 4 controls the heating means 24 to heat the particulate matter deposition portion 22 to 300° C.-800° C. during a cold start of the internal combustion engine 5 where the temperature of the exhaust gas detected by the temperature detection means 3 is lower than or equal 100° C.

Hereinafter, the configuration of the particulate matter detection apparatus according to the present example will be described in more detail.

As shown in FIG. 1, the particulate matter detection apparatus 1 is provided for detecting the particulate matter 6 contained in the exhaust gas that is emitted, via an exhaust pipe 53, from the internal combustion engine 5 installed in a motor vehicle. In the present example, the internal combustion engine 5 is a diesel engine equipped with a supercharger 51. Moreover, in the exhaust pipe 53 connected to the internal combustion engine 5, there is provided a purifying system 52 that includes a diesel oxidation catalyst 521 and a diesel particulate filter 522.

The particulate matter detection apparatus 1 includes: the particulate matter quantity detection means 2 that detects the quantity of the particulate matter 6 contained in the exhaust gas; the temperature detection means 3 that detects the temperature of the exhaust gas flowing through the exhaust pipe 53; and the control unit 4 that receives both the electrical signal outputted from the particulate matter quantity detection means 2 and the temperature information outputted from the temperature detection means 3.

The temperature detection means 3 is provided on the upstream side of the purifying system 52 in the exhaust pipe 53. The temperature detection means 3 is constituted of a temperature sensor that includes a temperature transducer. The temperature detection means 3 is configured to be capable of detecting the temperature of the exhaust gas flowing through the exhaust pipe 53. In addition, though the temperature of the exhaust gas is detected by the temperature detection means 3 in the present example, it may also be possible to detect the temperature of the exhaust pipe 53 by the temperature detection means 3.

Figure 3:
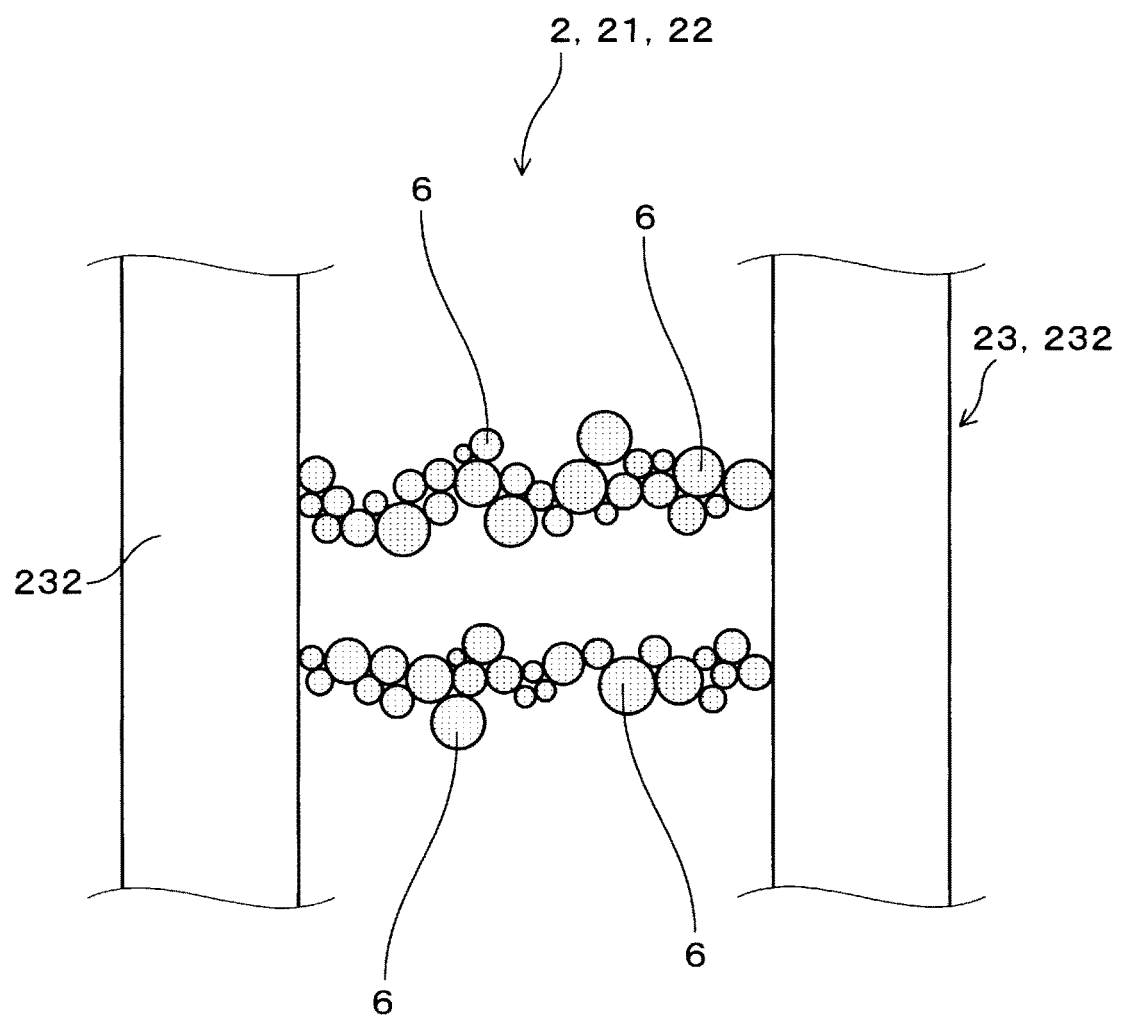
FIG. 3 is an enlarged view showing part of the particulate matter quantity detection means having particulate matter adhered thereto.

As shown in FIGS. 2 and 3, the particulate matter quantity detection means 2 is provided on the downstream side of the purifying system 52 in the exhaust pipe 53. The particulate matter quantity detection means 2 is a PM sensor which detects the quantity of the particulate matter 6. The particulate matter quantity detection means 2 includes a trap section 21 that traps part of the particulate matter 6 and the heating means 24 that heats the trap section 21.

The trap section 21 includes: the particulate matter deposition portion 22 that deposits the particulate matter 6 in the exhaust gas thereon; and the pair of opposite electrodes 23 arranged apart from each other on the particulate matter deposition portion 22. The particulate matter deposition portion 22 is shaped as a substantially rectangular plate. The particulate matter deposition portion 22 is formed of a ceramic material having electrical insulation properties. As the ceramic material, for example, alumina, zirconia, beryllia, mullite, silicon nitride or the like may be used. Moreover, the surface roughness of the particulate matter deposition portion 22 is 2.0 μm in ten-point average roughness. In the present example, the reference length of ten-point average roughness is set to 200 μm. Moreover, the reference length may also be set according to JIS B0633.

The pair of opposite electrodes 23 are formed of an electrically conductive material on the surface of the particulate matter deposition portion 22. The pair of opposite electrodes 23 each have an electrode base portion 231 formed parallel to a longitudinal direction of the particulate matter deposition portion 22 and a plurality of comb tooth portions 232 extending perpendicular to the longitudinal direction from the electrode base portion 231. The pair of opposite electrodes 23 are arranged so that: the electrode base portions 231 of the pair of opposite electrodes 23 face each other; and the comb tooth portions 232 of one of the pair of opposite electrodes 23 are interleaved with the comb tooth portions 232 of the other of the pair of opposite electrodes 23.

As shown in FIG. 3, when the particulate matter 6 is deposited on the particulate matter deposition portion 22 and an electrical conduction is established between the pair of opposite electrodes 23 by the particulate matter 6, the electrical resistance value between the pair of opposite electrodes 23 is lowered. A voltage is applied between the pair of opposite electrodes 23, and the amount of electric current flowing between the pair of opposite electrodes 23 as the electrical signal is changed with the change in the electrical resistance value between the pair of opposite electrodes 23. Consequently, the electric current value outputted from the particulate matter quantity detection means 2 to the control unit 4 is changed. That is, the electric current value outputted from the particulate matter quantity detection means 2 varies according to the deposition quantity of the particulate matter 6 on the particulate matter deposition portion 22, and thus carries information on the deposition quantity of the particulate matter 6. The control unit 4 includes a shunt resistor and outputs to an ECU (Engine Control Unit) a voltage that is calculated as the product of the outputted electric current value and the resistance value of the shunt resistor.

As shown in FIG. 2, the heating means 24 includes a heating coil 241 that generates heat upon being supplied with electric current from an electric power source, and a heating base portion 242 which is formed of an electrically insulative material and on which the heating coil 241 is provided. The heating means 24 is arranged to be stacked with the particulate matter deposition portion 22 on a side of the particulate matter deposition portion 22 opposite to the side where the pair of opposite electrodes 23 are arranged. The heating means 24 is configured to perform a preliminary heating for the particulate matter deposition portion 22 during a cold start of the internal combustion engine 5 and a high-temperature heating for removing the particulate matter 6 trapped by the trap section 21.

The temperature of the preliminary heating may be set to 300° C.-800° C. In the present example, the temperature of the preliminary heating is set to 500° C. The preliminary heating is performed in a state where the temperature of the exhaust gas detected by the temperature detection means 3 is lower than or equal to 100° C.

Moreover, the temperature of the high-temperature heating is set to 800° C. The high-temperature heating is performed, after detection of the deposition quantity of the particulate matter 6 or when the operation of the internal combustion engine 5 is stopped without a sufficient amount of the particulate matter 6 deposited on the particulate matter deposition portion 22, at a timing before newly depositing the particulate matter 6 on the particulate matter deposition portion 22.

In the present example, the control unit 4 performs control of the heating by the heating means 4, calculation of the deposition quantity of the particulate matter 6 on the particulate matter deposition portion 22 based on the output of the electrical signal, and calculation of the total emission quantity of the particulate matter 6 emitted from the internal combustion engine 5 during the trapping period.

Figure 4:
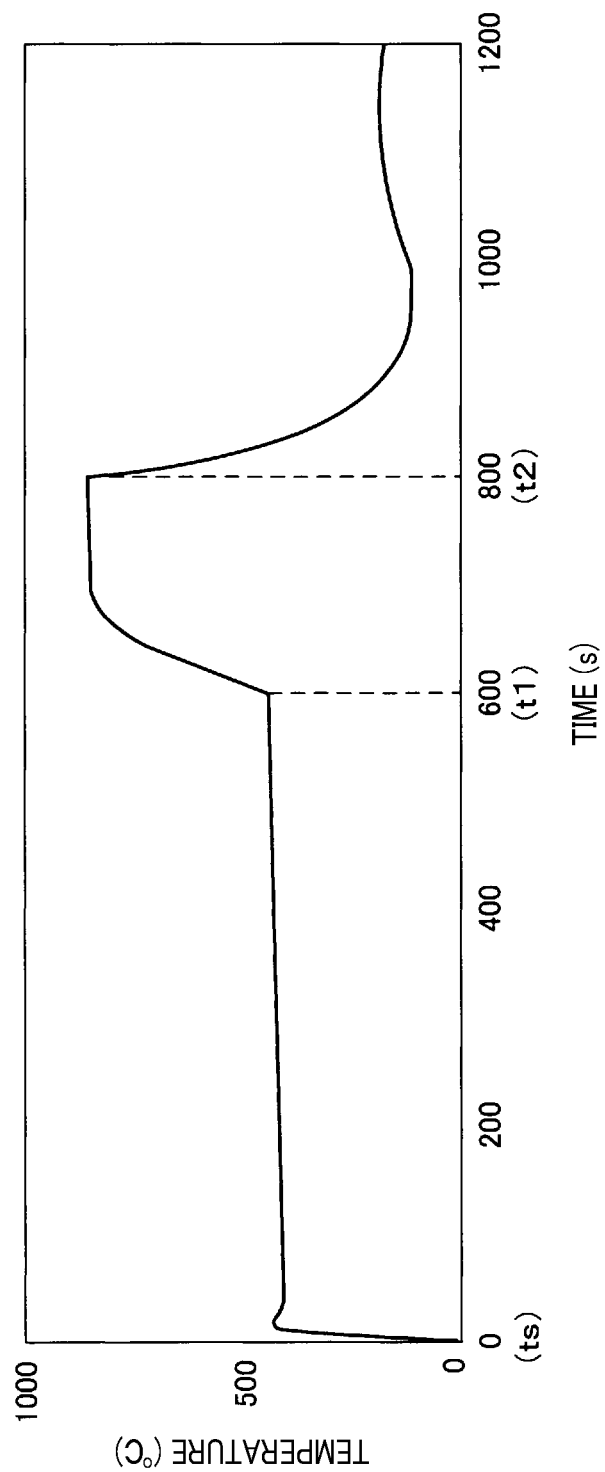
FIG. 4 is a graph showing heating temperature and heating time by a heating means in the particulate matter detection apparatus according to the example.

As shown in FIG. 4, in the present example, the control of the heating means 24 by the control unit 4 is performed using the temperature information detected by the temperature detection means 3. FIG. 4 is a graph whose horizontal axis indicates operation time of the internal combustion engine and whose vertical axis indicates heating temperature at the heating means 24. At the time (ts) when the internal combustion engine 5 is started, the temperature of the exhaust gas emitted from the internal combustion engine 5 is detected by the temperature detection means 3. At this time, if the temperature of the exhaust gas is lower than or equal to 100° C., the control unit 4 determines that the start of the internal combustion engine 5 is a cold start and sets the heating means 24 in the preliminary heating state. Then, for a time period from the start of the internal combustion engine 5 until a predetermined operation time t1, the preliminary heating of the particulate matter deposition portion 22 by the heating means 24 is continued. In the present example, the predetermined operation time t1 is set to 600 s. After the predetermined operation time t1 of 600 s, the preliminary heating by the heating means 24 is completed. In the present example, upon the completion of the preliminary heating, the heating means 24 is set to the high-temperature heating state to burn off the particulate matter 6 deposited on the particulate matter deposition portion 22. When the burning-off of the particulate matter 6 on the particulate matter deposition portion 22 is completed at an operation time t2, the heating by the heating means 24 is stopped and the trapping of the particulate matter 6 in the trap section 21 is started.

Moreover, the control unit 4 has both deposition quantity-related data and emission quantity-related data stored therein. The deposition quantity-related data indicate the relationship between the output of the electrical signal and the deposition quantity of the particulate matter 6 on the particulate matter deposition portion 22. The emission quantity-related data indicate the relationship between the deposition quantity of the particulate matter 6 on the particulate matter deposition portion 22 and the total emission quantity of the particulate matter 6 contained in the exhaust gas. Both the deposition quantity-related data and the emission quantity-related data are obtained in advance by performing a confirmation test in the internal combustion engine 5. The control unit 4 calculates, based on the output of the electrical signal, the deposition quantity of the particulate matter 6 using the deposition quantity-related data. Then, based on the calculated deposition quantity, the control unit 4 further calculates the total emission quantity of the particulate matter 6 using the emission quantity-related data. Consequently, the calculated total emission quantity of the particulate matter 6 is outputted by the control unit 4.

Next, advantageous effects of the present example will be described.

In the particulate matter detection apparatus 1, the control unit 4 controls the heating means 24 to heat the particulate matter deposition portion 22 to 300° C.-800° C. during a cold start of the internal combustion engine 5. Consequently, it is possible to suppress water-induced cracking and the adherence of condensate water in the particulate matter quantity detection means 2. That is, by heating the particulate matter deposition portion 22 to 300° C.-800° C., it is possible to cause the Leidenfrost effect between the particulate matter deposition portion 22 and the condensate water.

Therefore, when the particulate matter deposition portion 22 is exposed to water, due to the Leidenfrost effect, the particulate matter deposition portion 22 and the condensate water will not make contact with each other and the condensate water will slip off the particulate matter deposition portion 22. Hence, it is possible to prevent the condensate water from adhering to the particulate matter deposition portion 22 and thus possible to suppress the particulate matter deposition portion 22 from being suddenly cooled by adherence of the condensate water thereto. Consequently, it is possible to suppress various components included in the condensate water from adhering to the particulate matter deposition portion 22 as residues and water-induced cracking from occurring in the particulate matter deposition portion 22.

Moreover, the particulate matter quantity detection means 2 varies the output of the electrical signal according to change in the electrical resistance between the pair of opposite electrodes 23. The particulate matter quantity detection means 2 that is of an electrical resistance type using change in the electrical resistance value between the pair of opposite electrodes 23 has higher detection accuracy of the particulate matter 6 and less variation than particulate matter quantity detection means 2 of other types. Consequently, it is possible to further improve the accuracy of detecting the deposition quantity of the particulate matter 6.

Moreover, the heating of the particulate matter deposition portion 22 by the heating means 24 is continued until the elapse of a predetermined operation time t1 from the start time is of the internal combustion engine 5. Consequently, by continuing the heating until the predetermined operation time t1 at which condensate water is no longer produced in the exhaust gas, it is possible to reliably prevent the adherence of condensate water to the particulate matter deposition portion 22.

Moreover, though the timing of the preliminary heating of the particulate matter deposition portion 22 by the heating means 24 is controlled according to the operation time in the present example, the timing may also be controlled according to the temperature of the exhaust gas or the exhaust pipe. Specifically, the preliminary heating may be continued from the start of the internal combustion engine 5 until the temperature of the exhaust gas detected by the temperature detection means 3 exceeds 100° C. or until the temperature of the exhaust pipe 53 detected by the temperature detection means 3 exceeds 60° C. In this case, since the heating is continued until the temperature of the exhaust gas or the exhaust pipe 53 is increased to a temperature at which condensate water is no longer produced in the exhaust gas, it is possible to reliably prevent water-induced cracking and the adherence of condensate water in the particulate matter deposition portion 22.

Moreover, the particulate matter deposition portion 22 is formed of a ceramic material. Consequently, it is possible to improve the heat resistance of the particulate matter deposition portion 22 and more reliably prevent the adherence of condensate water during the heating of the particulate matter deposition portion 22.

Moreover, the surface roughness Rz of the particulate matter deposition portion 22 is set so that $0.01\ \mu m \leq Rz \leq 4.0\ \mu m$ in ten-point average roughness. Consequently, it is possible to more reliably prevent the adherence of condensate water to the particulate matter deposition portion 22. In addition, if the surface roughness Rz was set to be less than 0.01 μm, it would be advantageous to prevention of the adherence of condensate water; however, it might be impossible to obtain the desired surface roughness by processing. On the other hand, if the surface roughness Rz was set to be greater than 4.0 μm, the contact angles between the condensate water and the particulate matter deposition portion 22 would become large, increasing the wettability; consequently, it might be impossible to cause the Leidenfrost effect.

As above, the particulate matter detection apparatus 1 according to the present example can suppress water-inducted cracking and the adherence of residues in the particulate matter quantity detection means 2.

(Conformation Test 1)

In this confirmation test, the presence or absence of residues and water-induced cracking was confirmed while changing the heating temperature by the heating means 24.

In the confirmation test for residues, in the particulate matter quantity detection means 2 illustrated in the above example, the heating temperature of the heating means 24 was set in the range of 100° C.-900° C. at intervals of 100° C., and condensate water was dropped on the particulate matter deposition portion 22 heated to each temperature. In addition, the condensate water included impurities, such as $Mn(NO_3)_2$, $MgSO_4$ or the like, by about 6 w %. The dropping quantity of the condensate water was set to two patterns of 1 μl and 2 μl.

After dropping the condensate water on the particulate matter deposition portion 22, the presence or absence of residues was confirmed by performing a component analysis on the surface of the particulate matter deposition portion 22. In the evaluation about residues on TABLE 1, [◎] indicates that residues were detected at neither of 1 μl and 2

μl. [○] indicates that residues were detected at 2 μl, but not at 1 μl. [X] indicates that residues were detected at each of 1 μl and 2 μl.

In the confirmation test for water-induced cracking, as in the confirmation test for residues, in the particulate matter quantity detection means 2 illustrated in the above example, the heating temperature of the heating means 24 was set in the range of 100° C.-900° C. at intervals of 100° C., and condensate water was dropped on the particulate matter deposition portion 22 heated to each temperature. The dropping quantity of the condensate water was set to two patterns of 1 μl and 1.5 μl.

Ten test samples were prepared for each temperature. After dropping the condensate water on the particulate matter deposition portion 22, the presence or absence of water-induced cracking was confirmed. In each test sample, the surface roughness of the particulate matter deposition portion 22 was set to 4.0 μm in ten-point average roughness. Moreover, the reference length of ten-point average roughness was set to 200 μm.

In the evaluation about water-induced cracking on TABLE 1, [◎] indicates that water-induced cracking was confirmed at neither of 1 μl and 1.5 μl. [○] indicates that water-induced cracking was confirmed in at least one test sample at 1.5 μl, but not at 1 μl. [X] indicates that water-induced cracking was confirmed in at least one test sample at each of 1 μl and 2 μl.

Moreover, in the total evaluation on TABLE 1, [◎] indicates that both the evaluation about residues and the evaluation about water-induced cracking resulted in [◎]. [○] indicates that one of the evaluation about residues and the evaluation about water-induced cracking resulted in [◎], while the other resulted in [○]. [X] indicates that either of the evaluation about residues and the evaluation about water-induced cracking resulted in [X].

TABLE 1

| TEMPERATURE | RESIDUES | WATER-INDUCED CRACKING | TOTAL EVALUATION |
|---|---|---|---|
| 100° C. | X | ◎ | X |
| 200° C. | X | ◎ | X |
| 300° C. | ○ | ◎ | ○ |
| 400° C. | ◎ | ◎ | ◎ |
| 500° C. | ◎ | ◎ | ◎ |
| 600° C. | ◎ | ◎ | ◎ |
| 700° C. | ◎ | ◎ | ◎ |
| 800° C. | ◎ | ○ | ○ |
| 900° C. | ◎ | X | X |

As shown on TABLE 1, in the confirmation test for residues, when the heating temperature in the heating means 24 was 300° C.-900° C., no residue was confirmed after 1 μl of the condensate water was dropped. Moreover, when the heating temperature in the heating means 24 was 400° C.-900° C., no residue was confirmed after 2 μl of the condensate water was dropped. That is, it has been confirmed that by setting the heating temperature in the heating means 24 to 300° C.-900° C., it was possible to suppress the adherence of residues. Moreover, it also has been confirmed that by setting the heating temperature in the heating means 24 to 400° C.-900° C., the effect of suppressing the adherence of residues was improved so that even when the condensate water was dropped more, it was still possible to suppress the adherence of residues.

Moreover, in the confirmation test for water-induced cracking, when the heating temperature in the heating means 24 was in the range of 100° C.-800° C., no water-induced cracking was confirmed with 1 μl of the condensate water dropped. Moreover, when the heating temperature in the heating means 24 was in the range of 100° C.-700° C., no water-induced cracking was confirmed with 1.5 μl of the condensate water dropped. That is, it has been confirmed that by setting the heating temperature in the heating means 24 to 100° C.-800° C., it was possible to suppress occurrence of water-induced cracking. Moreover, it also has been confirmed that by setting the heating temperature in the heating means 24 to 100° C.-700° C., the effect of suppressing occurrence of water-induced cracking was improved so that even when the condensate water was dropped more, it was still possible to suppress occurrence of water-induced cracking.

As above, by setting the heating temperature in the heating means 24 to be in the range of 300° C.-800° C., it is possible to achieve both the effect of suppressing the adherence of residues and the effect of suppressing occurrence of water-induced cracking. Moreover, by setting the heating temperature in the heating means 24 to be in the range of 400° C.-700° C., it is possible to further improve both the effect of suppressing the adherence of residues and the effect of suppressing occurrence of water-induced cracking.

(Conformation Test 2)

In this confirmation test, the presence or absence of residues was confirmed while changing the surface roughness of the particulate matter deposition portion 22.

In the confirmation test for residues, a plurality of particulate matter quantity detection means were used whose surface roughnesses Rz were respectively set to 2.0 μm, 2.5 μm, 4.0 μm, 4.5 μm and 5.0 μm. In each particulate matter quantity detection means, the heating temperature of the heating means 24 was set at intervals of 50° C. in the range of 250° C.-500° C. and at intervals of 100° C. in the range of 500° C.-800° C., and condensate water was dropped on the particulate matter deposition portion 22 heated to each temperature. In addition, the condensate water included Mn by about 6 w %. The dropping quantity of the condensate water was set to 0.3 μl.

TABLE 2

| | | SURFACE ROUGHNESS Rz | | | | |
|---|---|---|---|---|---|---|
| | | 2.0 | 2.5 | 4.0 | 4.5 | 6.0 |
| HEATING TEMPERATURE (° C.) | 800 | ○ | ○ | ○ | ○ | ○ |
| | 700 | ○ | ○ | ○ | ○ | ○ |
| | 600 | ○ | ○ | ○ | ○ | ○ |
| | 500 | ○ | ○ | ○ | ○ | ○ |
| | 450 | ○ | ○ | ○ | ○ | ○ |
| | 400 | ○ | ○ | ○ | ○ | ○ |
| | 350 | ○ | ○ | ○ | ○ | ○ |
| | 300 | ○ | ○ | ○ | X | X |
| | 250 | X | X | X | X | X |

After dropping the condensate water on the particulate matter deposition portion 22, the presence or absence of residues was confirmed by performing a component analysis on the surface of the particulate matter deposition portion 22, and the presence or absence of a short circuit between the electrodes was confirmed. TABLE 2 shows the test results at each temperature and each surface roughness Rz. On TABLE 2, [○] indicates that neither residues nor a short circuit between the electrodes was confirmed. [X] indicates that either or both of residues and a short circuit between the electrodes was confirmed.

When the heating temperature was in the range of 350° C.-800° C., residues and a short circuit between the electrodes were confirmed at none of the surface roughnesses Rz. Moreover, when the heating temperature was 300° C., residues and a short circuit between the electrodes were not confirmed at the surface roughnesses Rz less than or equal to 4.0 μm. When the heating temperature was 250° C., at least one of residues and a short circuit between the electrodes was caused at each surface roughness Rz.

As above, by setting the surface roughness Rz to be less than or equal to 4.0 μm, it is possible to more reliably achieve the effect of suppressing the adherence of residues when the heating temperature is in the range of 300° C.-800° C. Moreover, it is preferable for the surface roughness Rz to be as small as possible in the range of less than or equal to 4.0 μm; however, in terms of productivity, it is also preferable for the surface roughness Rz to be greater than or equal to 0.01 μm.

DESCRIPTION OF REFERENCE SIGNS

1: particulate matter detection apparatus
2: particulate matter quantity detection means
22: particulate matter deposition portion
23: opposite electrodes
24: heating means
3: temperature detection means
4: control unit
5: internal combustion engine
53: exhaust gas
6: particulate matter

The invention claimed is:

1. A particulate matter detection apparatus comprising:
a particulate matter quantity detection means including a particulate matter deposition portion that deposits thereon part of particulate matter contained in exhaust gas emitted from an internal combustion engine and a pair of opposite electrodes arranged apart from each other on the particulate matter deposition portion, the particulate matter quantity detection means varying output of an electrical signal according to change in electrical characteristics caused by the deposition of the particulate matter on the particulate matter deposition portion;
a temperature detection means that detects temperature of the exhaust gas or an exhaust pipe through which the exhaust gas flows;
a control unit that determines a deposition quantity of the particulate matter on the particulate matter deposition portion based on the electrical signal outputted by the particulate matter quantity detection means and receives information on the temperature of the exhaust gas or the exhaust pipe detected by the temperature detection means; and
a heating means for heating the particulate matter deposition portion,
wherein
the control unit controls the heating means to heat the particulate matter deposition portion to 300° C.-800° C. during a cold start of the internal combustion engine where the temperature of the exhaust gas detected by the temperature detection means is lower than or equal 100° C. or the temperature of the exhaust pipe detected by the temperature detection means is lower than or equal 60° C., and
the control unit is configured to start, upon the internal combustion engine being started, the heating of the particulate matter deposition portion by the heating means.

2. The particulate matter detection apparatus as set forth in claim 1, wherein the particulate matter quantity detection means varies the output of the electrical signal according to change in electrical resistance between the pair of opposite electrodes.

3. The particulate matter detection apparatus as set forth in claim 1, wherein the heating of the particulate matter deposition portion by the heating means is continued until elapse of a predetermined operation time from the start of the internal combustion engine.

4. The particulate matter detection apparatus as set forth in claim 1, wherein the particulate matter deposition portion is formed of a ceramic material.

5. The particulate matter detection apparatus as set forth in claim 1, wherein a surface roughness of the particulate matter deposition portion is set so that 0.01 μm≤Rz≤4.0 μm in ten-point average roughness.

* * * * *